United States Patent [19]
de Sterke

[11] 4,375,165
[45] Mar. 1, 1983

[54] SYSTEM FOR INSPECTING WELDED JOINTS IN PIPE LINES BY MEANS OF ULTRASONIC WAVES

[75] Inventor: Arie de Sterke, Vlaardingen, Netherlands

[73] Assignee: Rontgen Technische Dienst B.V., Rotterdam, Netherlands

[21] Appl. No.: 162,750

[22] Filed: Jun. 25, 1980

[30] Foreign Application Priority Data

Jun. 26, 1979 [NL] Netherlands .......................... 7904973

[51] Int. Cl.$^3$ ............................................. G01N 29/04
[52] U.S. Cl. ........................................ 73/622; 73/637
[58] Field of Search ................. 73/612, 614, 615, 618, 73/620, 622, 625, 626, 628, 637, 638, 640

[56] References Cited

U.S. PATENT DOCUMENTS

| | | | |
|---|---|---|---|
| 3,213,676 | 10/1965 | Makous | 73/611 |
| 3,326,037 | 6/1967 | Stewart | 73/620 |
| 3,805,597 | 4/1974 | Ohta et al. | 73/612 |
| 3,921,440 | 11/1975 | Toth | 73/622 |
| 3,942,358 | 3/1976 | Pies | 73/624 |
| 4,131,026 | 12/1978 | Ries et al. | 73/638 |
| 4,147,065 | 4/1979 | Lather et al. | 73/615 |
| 4,173,898 | 11/1979 | Förstermann et al. | 73/612 |
| 4,270,389 | 6/1981 | Shiraiwa et al. | 73/622 |

FOREIGN PATENT DOCUMENTS

2373058 6/1978 France .................................. 73/622

OTHER PUBLICATIONS

D. H. Turner et al., "An Ultrasonic Bracelet Probe Device for Inspection of Tube Butt Welds", Ultrasonics for Industry, pp. 51-55, 1969.

*Primary Examiner*—Stephen A. Kreitman
*Attorney, Agent, or Firm*—Brumbaugh, Graves, Donohue & Raymond

[57] ABSTRACT

An ultrasonic flaw detection system is used for inspecting circumferentially welded joints in a pipeline. The ultrasonic probes include crystals for directing and receiving longitudinal waves reflected from the pipe interior surface in order to measure the pipe thickness. A gating device is timed on the basis of the measured pipe thickness and enables the angled crystals to receive transverse ultrasonic waves from weld defects and avoids recording reflections due to weld geometry. In addition a manipulation device having a guide band positioned around the pipe and an eccentric movable toward and away from the band may be used for clamping the carriage to the band.

11 Claims, 10 Drawing Figures

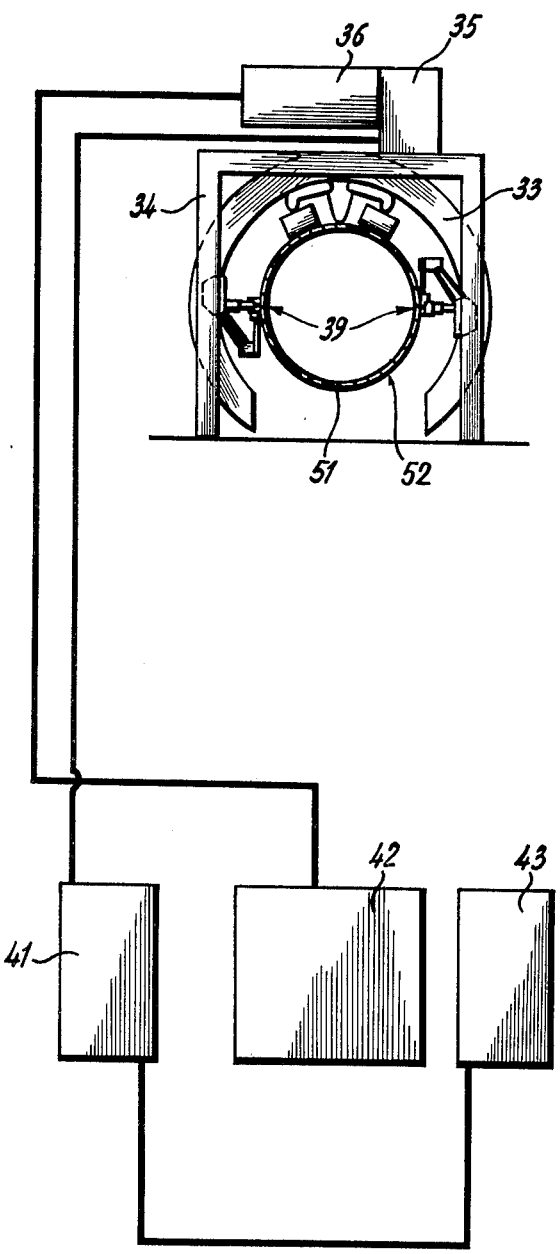

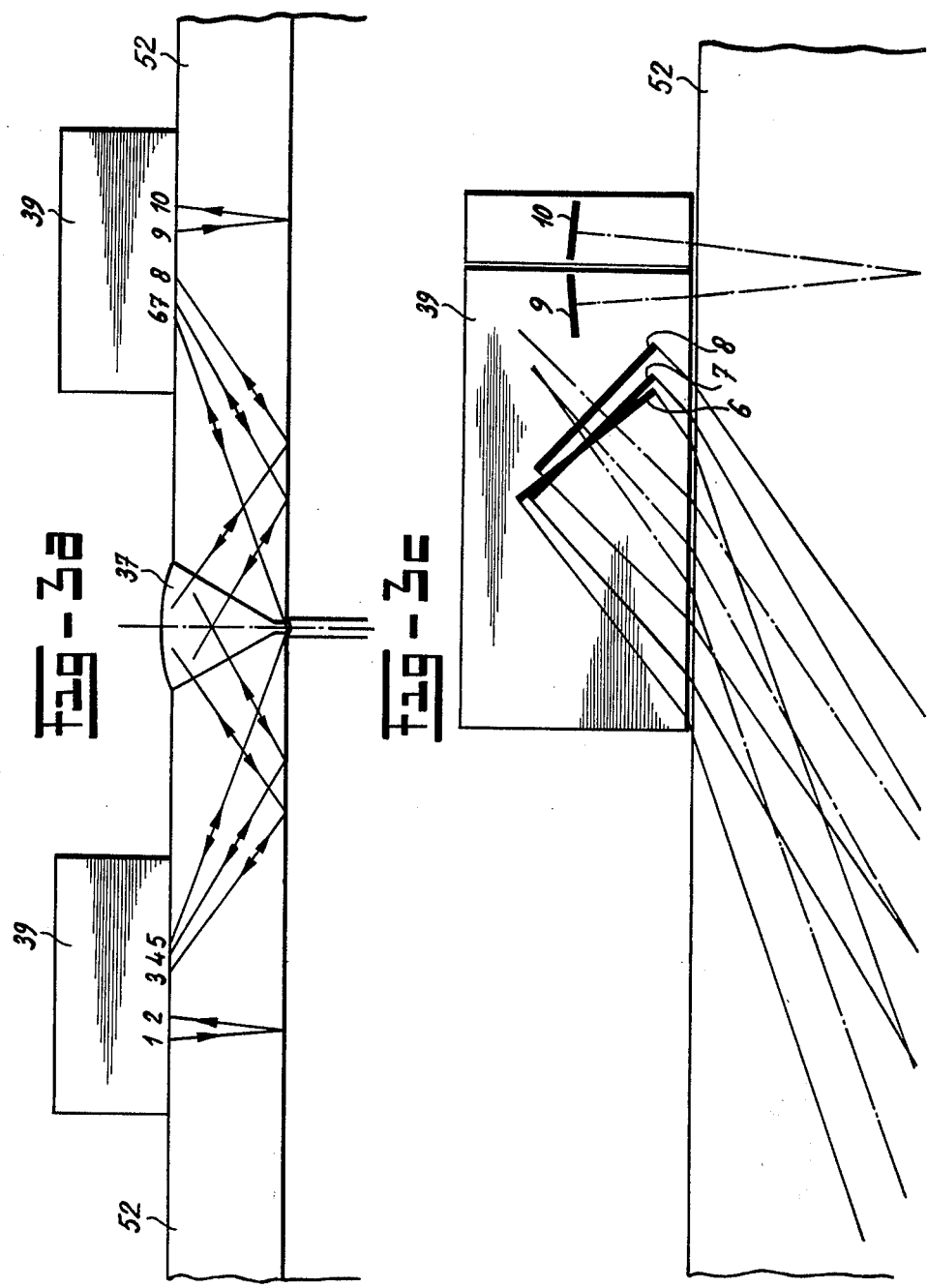

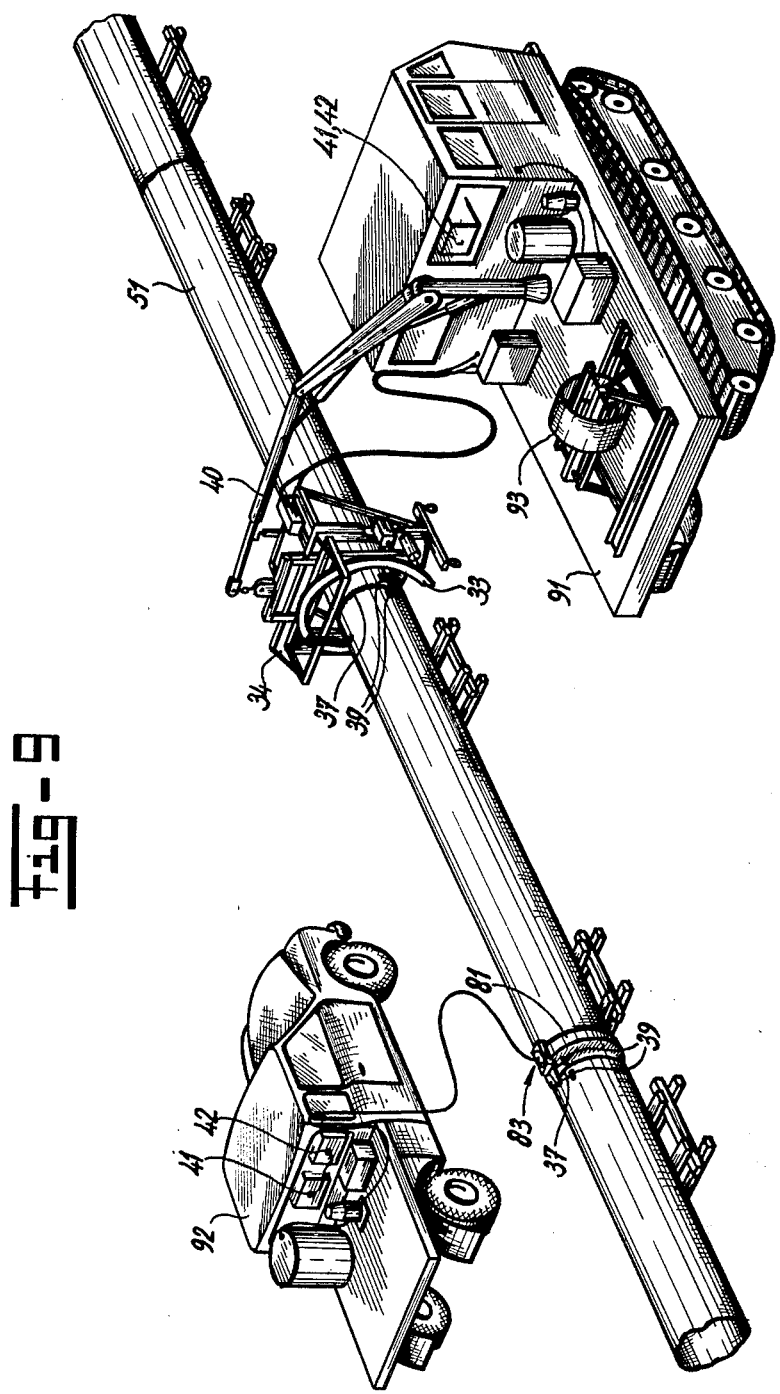

SYSTEM FOR INSPECTING WELDED JOINTS IN PIPE LINES BY MEANS OF ULTRASONIC WAVES

BACKGROUND OF THE INVENTION

The present invention relates to a system for inspecting circumferential welded joints in pipe lines etc., using ultrasonic waves. Prior art systems of this type are known. It is during the construction of pipe lines for transporting, for instance, gas and oil extremely important that all the security requirements presented by the authorities are met.

Therefore it is necessary to inspect the welded joints with the utmost reliability. Furthermore such inspection should be carried out fast in order not to delay the pipe laying operations. That applies both to the construction of pipe lines on land and to the construction of pipe lines on the sea bottom. Until now the welded joints between the pipe sections have been examined radiografically. As a result of the rather restricted detection sensitivity of said radio graphic method for two-dimensional defects, for instance cracks or lack of side wall fusion, one has looked for other methods such as magnetic crack detection and for ultrasonic testing. Especially ultrasonic testing has a number of advantages. It is for instance possible to use relatively light weight and handy apparatusses and to inspect materials with greater thickness. Furthermore there is no radiation danger, an increased detection sensitivity for two-dimensional defects, an easier depth determination of defects, the possibility to mechanize the ultrasonic scanning with related registration, and there is no need to introduce a device into the pipe line. Especially with the mechanized ultrasonic method, the examination time does not necessarily increase with the wall thickness, as is the case when using radiagrafical methods.

BRIEF SUMMARY OF THE INVENTION

An object of the invention is to provide a system for mechanically inspecting ccircumferential welded joints in pipe lines using ultrasonic waves, which system should be mobile, suitable for use on land or on board pipe laying vessels and adapted to different pipe diameters, wall thicknesses and welding methods.

Furthermore it must be possible to register quickly the position and the lack of all unacceptable defects in the welded joints. Said registration should be produced during the scanning. Also the system should be operating fast corresponding to the requirements on board pipe laying vessels. The invention now provides a system for inspecting circumferentially welded joints in pipe lines using ultrasonic waves, comprising a multichannel ultrasonic device with multicrystal switch, a manipulator with control unit and at least a set of ultrasonic probes and a recorder. The manipulator is configured approximately circularly and adapted to be positioned around the pipe line. The set of ultrasonic propes is attached to said manipulator such that said probes are pressed against the outer pipe wall near the welded joint and are moved around the pipe, guided by the manipulator, whereby the crystals in each ultrasonic probe are activated through the multicrystal switch controlled by the multichannel ultrasonic device for transmitting ultrasonic waves into the pipe material and for receiving reflected waves, which reflected waves are processed by the ultrasonic device and registered by the recorder.

The invention will be explained in more detail with reference to the accompanying drawings.

BRIEF DESCRIPTION OF THE DRAWINGS

FIG. 2 shows schematically the components of the total system according to the invention.

FIG. 3a shows in a sectional view perpendicular to the welding direction an example of the configuration of the ultrasonic waves generated by the different crystals.

FIG. 3c shows an example of the crystals of a probe and the ultrasonic waves they propagate.

FIG. 4 shows a top view of the configuration in FIG. 3a.

FIG. 8b is a top plan view of the manipulator example of FIG. 8a.

FIG. 9 shows a survey of the two manipulator embodiments, one of the horse shoe type and one of the band type which manipulators are adapted for use in practise for inspecting an over land pipe line.

DESCRIPTION OF PREFERRED EMBODIMENT

Figure 1:
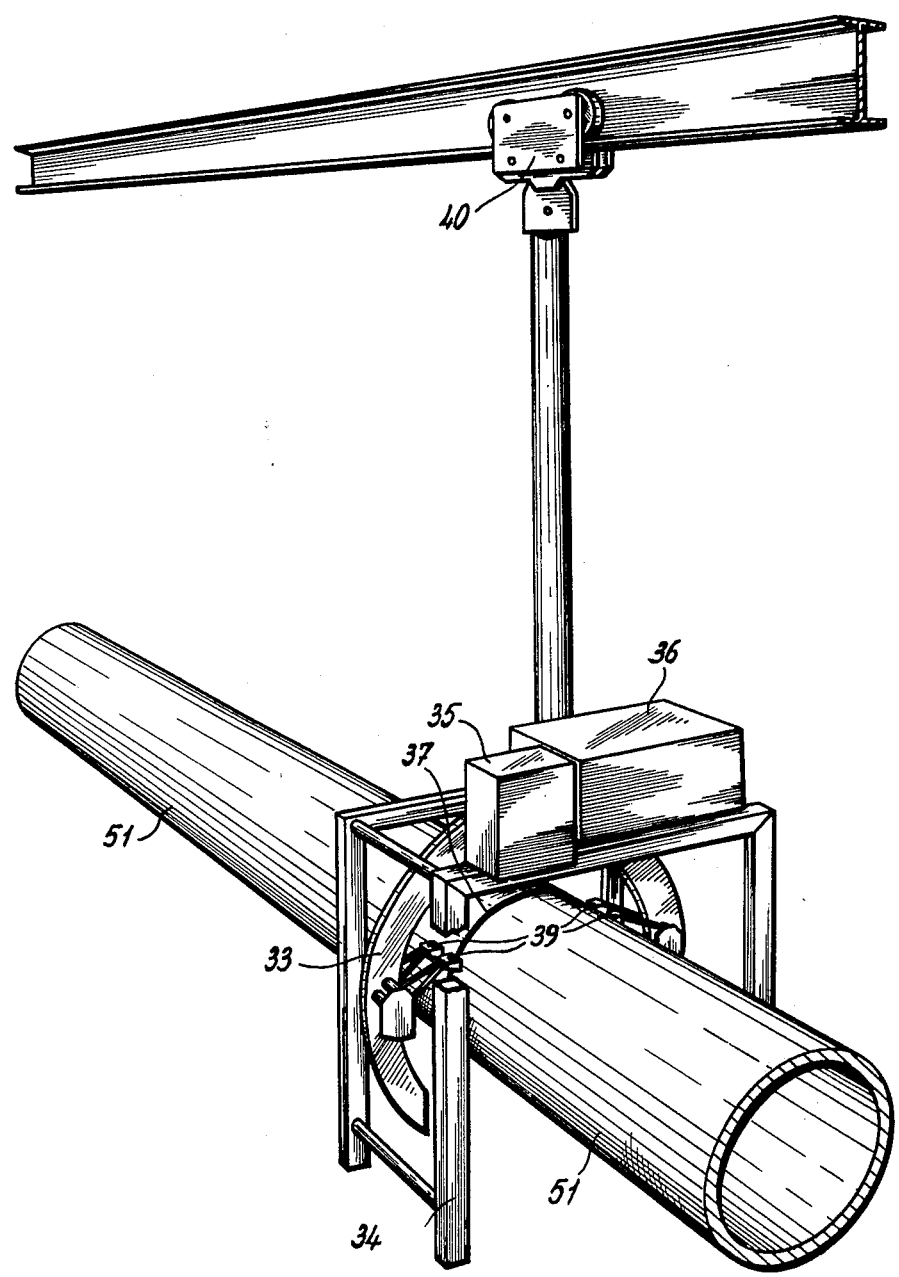
FIG. 1 shows a schematical view of some components of the system positioned for inspection around a welded joint on board of a pipe laying vessel or on land.

FIG. 1 shows a schematic view of a manipulator positioned around the pipe line 51. The manipulator 33 may have an interrupted circular configuration of the so called horse shoe type fitted into a frame 34. The frame 34 carries the auxiliary control unit 35 for activating the manipulator and the multi crystal switch 36. Said auxiliary control unit can be operated on the spot by the investigating personnel. The manipulator is rotated around the pipe line over 180° with a possible additional overlap of 10°. That is sufficient to investigate the total joint length along the circumference of the pipe, because ultrasonic measuring heads or probes 39 are attached to both halves or legs of the manipulator. The frequency of the ultrasonic waves transmitted by the crystals in said measuring probes is for instance 4 MHz.

The manipulator 33 is operated fully electrically, but partially pneumatic, hydraulic or mechanical operation is also possible.

After positioning of the manipulator 33 around the joint 37 using for instance the hoisting equipment 40, the manipulator is fixed to the pipe by means of an electrical, pneumatical, hydraulic or mechanically operated clamp. Thereafter the horse shoe shaped part of the manipulator is brought into the plane of the joint. Also electrical, pneumatic, hydraulic or mechanical operation is possible. During this set up step the weld bead 37 can be used as reference, but it is also possible to indicate a reference line parallel to the weld before the welded joint is made. During the inspection, the position of the probes 39 can be read from the main control unit 41 of the manipulator 33 and also from the recording paper.

In FIG. 2 most of the components of the system are illustrated schematically. Two probes 39 are attached each to a leg of the manipulator 33 through a supporting element such that the probes are, referring to the center line of the pipe, diametrically positioned against the outer pipe wall 52 at both sides of the welded joint. The multi-crystal switch 36 and the auxiliary control unit 35 are connected through electrical cables respectively to the multi-channel ultrasonic device 42, for instance positioned in a remote measuring station and the main control unit 41. The main control unit may comprise a built in recorder and/or may have an other connection to a separate recorder 43.

FIG. 3a illustrates in which way in each of the probes 39 pressed against the outside of the pipe wall, a number of crystals is contained. The configuration of said crystals depends on the thickness of the pipe wall 52 and the shape of the weld. Each crystal has, dependent of its position and its slope in the probe housing its own direction for transmitting and receiving ultrasonic waves, so that the whole volume of the weld is inspected with sufficient sensitivity by a number of crystals. The height of the weld is thereto subdivided in a number of zones, for instance three or more zones.

The crystal-transmmitter/receiver combinations 1, 2 and 9, 10 are so called right angle crystals, which are transmitting longitudinal waves perpendicular to the pipe wall and receiving longitudinal waves reflected by the underside of the wall. This wall echo measurement or wall thickness measurement is used for the coupling adjustment, sensitivity adjustment and gate correction which will be discussed in more detail later on. The other crystals 3, 4, 5, 6, 7, 8 which are positioned in line, function as transmitter and as receiver. They are also called the angle crystals, because they are transmitting and receiving transverse waves under an angle with the pipe wall. The crystals 3, 8 out of this set are scanning the uppermost or shallow zone, the crystals 4, 7 are scanning the medium zone and the crystals 5, 6 are scanning the lowest or deepest zone. For a through-going transmission measurement, for instance for detection of defects which are at such unfavourable positions that only breaking at the inner surface of the weld bead can be observed the crystals 5 and 6 may be used. FIG. 3c shows furthermore in a detailed side view how the plate shaped crystals 6, 7, 8, 9, 10 are contained in the probe 39.

Figure 3B:
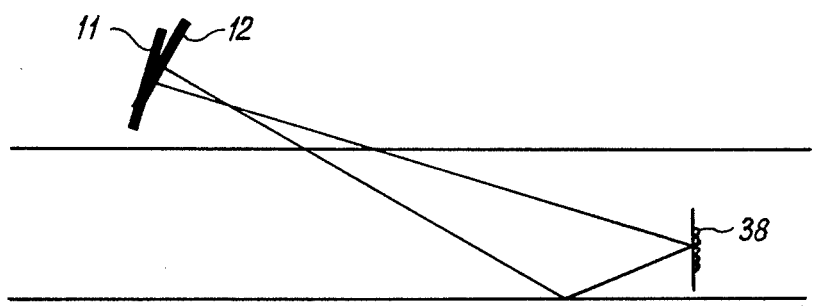
FIG. 3b shows an example of the transmission path of the ultrasonic wave beam in the pipe wall during the investigation for transverse defects in the joint.

In FIG. 3b an example is given of a set of crystals respectively functioning as transmitter (11) and receiver (12), whereby also the path of the ultrasonic wave reflecting against a discontinuity 38 transverse to the welding direction is indicated.

Figure 4:
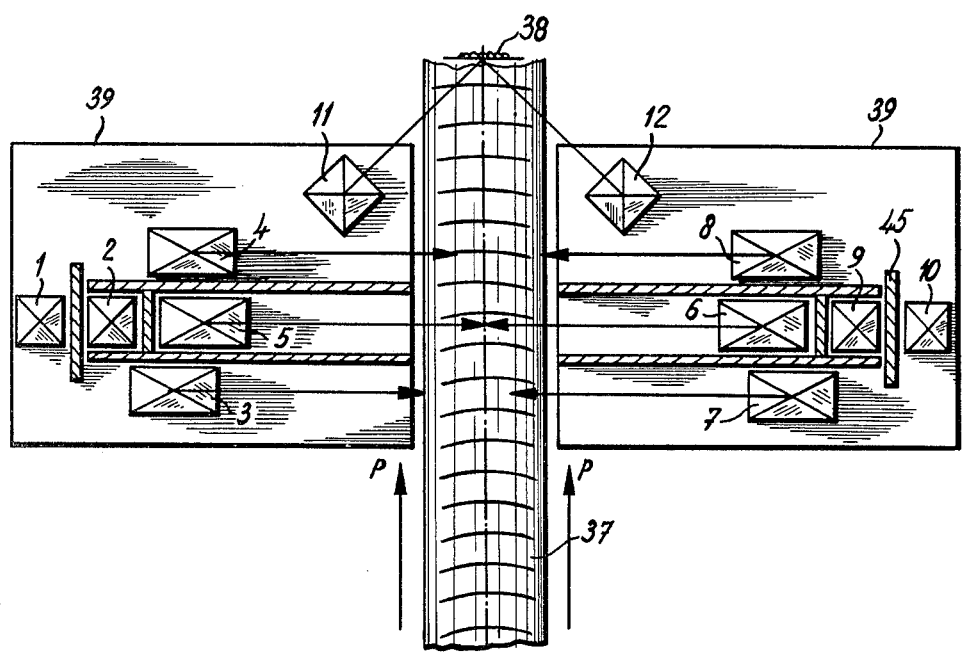

FIG. 4 shows a top view of the crystal configuration in the propes of FIG. 3a. The arrows P indicate in which direction the probes 39 are moving along the weld 37. In the direction of moving the crystals are mutually displaced. The shaded areas 45 represent acoustical shields in the probes so that the crystals are acoustically shielded mutually.

The crystals 11 and 12 are used for examining defects extending transversely of the weld 37, such as the defect 38, for instance, by reflection of the ultrasonic wave against the underside of the material (the inner pipe wall). Reference is also made to FIG. 3b.

The probes and the therein contained crystals are controlled through the multi crystal switch 36 by the multi channel ultrasonic device 42. Through the multi crystal switch the crystals are activated to transmit ultrasonic waves, which are after reflection at any disturbance or crack received by the same crystal or by another crystal and processed in the ultrasonic device and registered in the recorder. Said recorder may form part of the main control unit. The ultrasonic device is able to activate a maximum of for instance thirty-two different crystals in very fast sequential order. Controlled by the multichannel ultrasonic device the multi crystal switch assures that the probes are switched on and off at the right moments and in the desired combination. The control functions can be preprogrammed depending on the used inspection method.

The received error or fault signals can be divided based on the path they travel along in the material. To be able to separate error signals from possible form-echo's of the weld (that means that the echo signal is dependent on the form of the weld) only part of the time base is monitored for further processing. The monitored part of the time base is called the "gate". Only signals received in said gate are registered. Each crystal or combination of crystals corresponding to a channel of the multi-channel ultrasonic device has its own gate, which can be chosen separately for each channel. Also the gain for amplifying the received signals is adjustable per channel.

Figure 5:
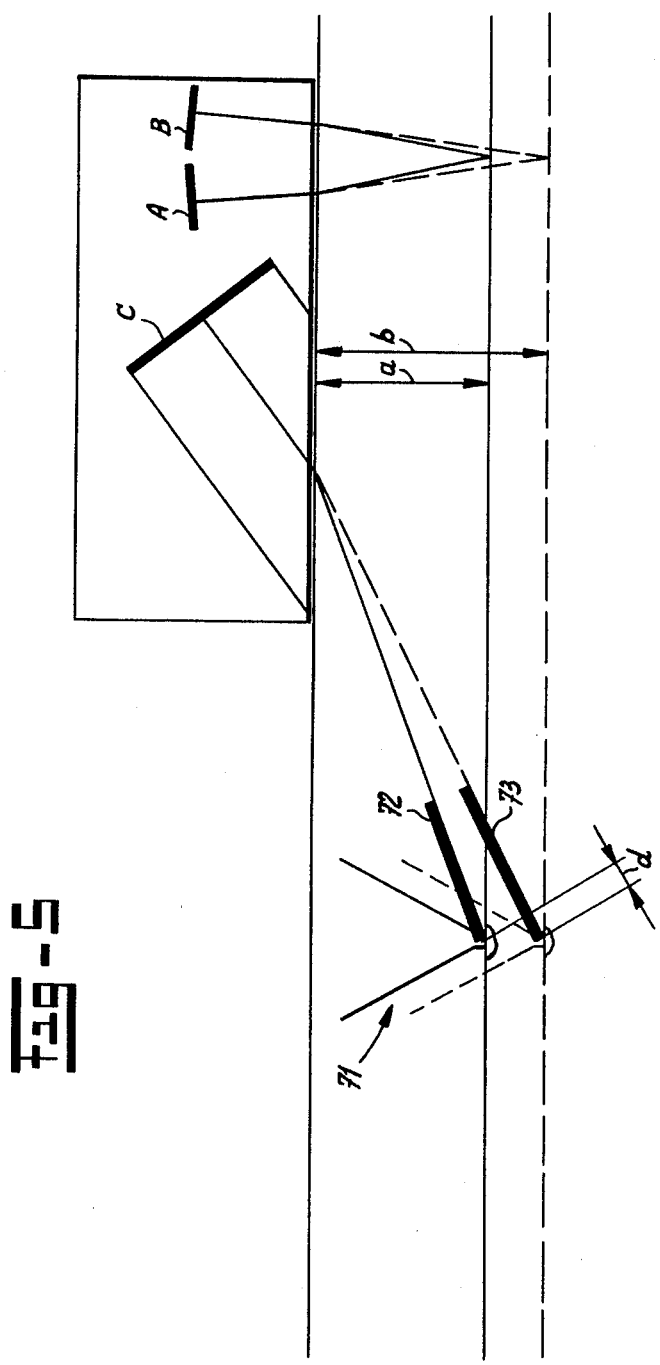
FIG. 5 illustrates schematically the function of the gate correction controlled by an ultrasonic measurement of the wall thickness.

FIG. 5 illustrates how the gate length of a measuring channel is controlled by the time, in which an ultrasonic wave, transmitted by the right angle crystals A, B, travels along the path to the inner wall of the pipe and back. Said gate correction appeared to be necessary because the pipe wall thickness is not constant but may vary within predetermined tolerances. In FIG. 5 the reference a indicates the minimum possible wall thickness and b indicates the maximum possible wall thickness. The travel time differences resulting from said wall thickness variation are measured by the right angle probe A, B and are translated, using a multiplication factor, in a correction for the gate length of the measuring channel. Said multiplication factor is dependent on the slope of the angled crystal C connected to the measuring channel concerned, and furthermore dependent on the ratio between the propagation speeds of the wave types transmitted by the right angle probe and the angled probes. The right angle probe transmits longitudinal waves and the angled probe transmits transverse waves. In FIG. 5 the reference 71 indicates an example of a weld shape. For measuring the weld shape and minimum wall thickness a, a gate 72 is adjusted and for measuring the weld shape at maximum wall thickness b, a somewhat larger gate 73 is adjusted. Both gates start at the same point of the time base. In FIG. 5, reference d indicates the gate extension. The value of said factor is previously known and may be programmed. Besides this gate correction, it is furthermore possible within certain limits to adjust the sensitivity of the measuring channels based on the prevailing sound transmission condition or coupling between the probe and the pipe wall dependent on the coupling means such as water between the probe and the rough pipe wall. Also in this case, the signal of the right angle probe may be used as reference. The basic sensitivity is adjusted for all measuring channels separately before the start of the inspection. For this calibration purpose artificial defects are used which defects are present in a specially prepared test segment. The type and dimensions of said defects are defined in the code of an inspection rule which may be used in consultation with the principal or printout made from the test segment.

The actual sensitivity and gate length are, as above mentioned, for the different measuring channels controlled by the control channels, i.e. the right angle channels, of which there are for instance four, positioned at four different places. By programming the ultrasonic device it is predetermined which measuring channels are controlling which control channels.

Figure 6:
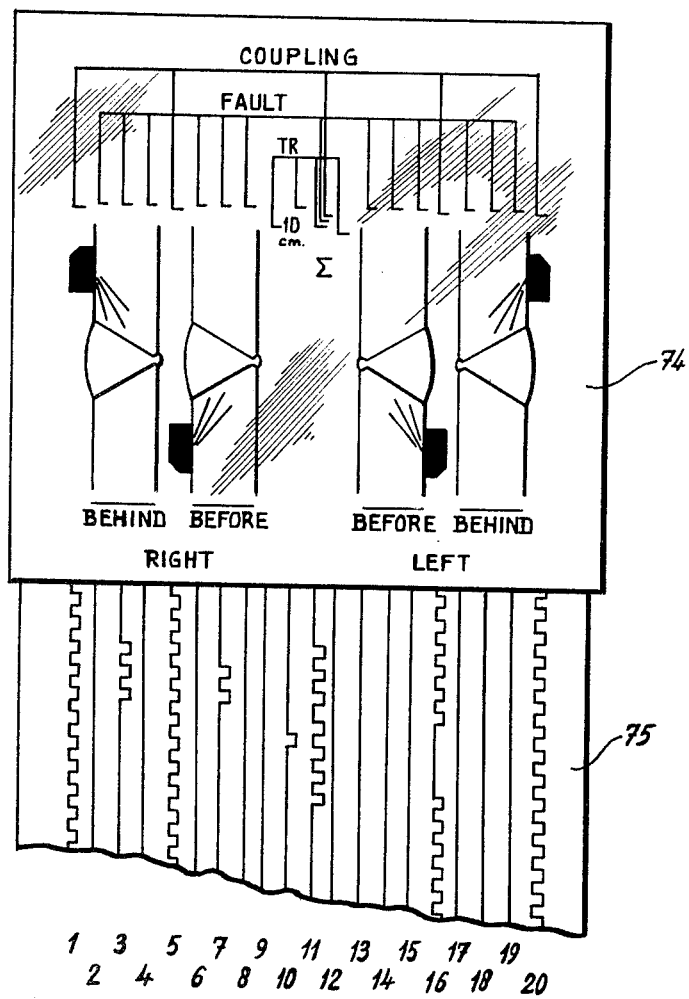
FIG. 6 illustrates an example of the recording made during the scanning of the joint.

FIG. 6 illustrates an interpretation mask 74, for instance a transparent mask fitted to the front of the recorder for simple reading. The recording paper 75 passes under said mask during the measurement and onto said paper for instance 20 channels are recorded. Onto the mask an example of a registration for a V-weld is indicated, whereby the weld height is divided into three zones (upper, middle and lower zone). The weld is examined from both sides. The left half of the recording corresponds to the set of probe which is moving along the upper side of the pipe line and the right halve of the recording corresponds with the set of probes moving along the under side of the pipe line. The length of the recording may one to one correspond to the length of the weld. As is indicated in the example each probe contains a channel for registering the ultrasonic coupling condition and a number of measuring channels, in this case three. The coupling condition is measured by means of the right angle crystal or a pair of right angle crystals contained in the probe, or by means of a transmission signal through the weld using two crystals, one of them in the one probe is used as transmitter and the other in the other probe is used as receiver.

It is also possible to register the signal from a right angle crystal to control the coupling and furthermore to register the signal transmitted through the weld. Said last mentioned signal may be used for additional error detection, i.e. detection of unfavourable positioned very big deviations, such as a crack through the weld, or a number of smaller sound shielding deviations, deviations that absorb or block rather than reflecting, such as, for example, many porous cavities. The center line of the recording is used to denote the position of the probes along the weld. The channel, indicated by є may be used as summing channel. The signals in this channel are formed as the sum of all the signals in the other channels. Underneath is indicated which registration functions are carried out in which channels 1–20:

channel 2-3-4-6-7-8-13-14-15-17-18-19: defect registrations channel 1-5-16-20: coupling monitoring channel 9-12: transmission channel 10: position channel 11: summation.

The recording is made according to the so called yes/no principle. That means that an echo signal is only recorded when the signal within the above mentioned gate exceeds a predetermined level. This level is previously adjusted corresponding to the inspection rule or code.

Figure 7A:
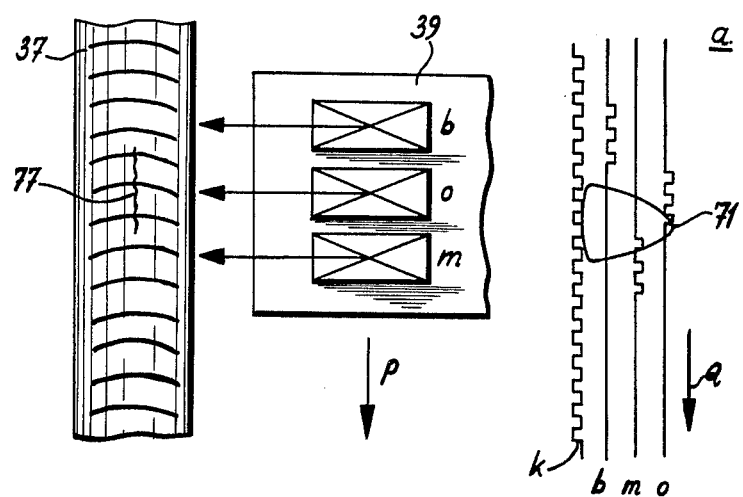
FIGS. 7a and b illustrate schematically the influence of the internal signal shift resulting in elimination of the spacial displacement of the crystals within the probe.
Figure 7B:
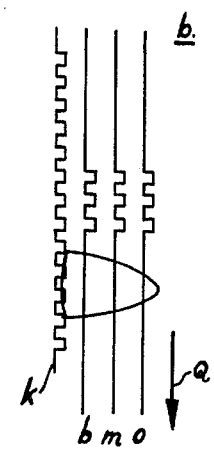

In FIGS. 7a and 7b the direction of movement of the probe 39 along the weld 37 is indicated by P and the direction of movement of the recording paper is indicated by Q. There are four channels recorded onto the paper, i.e. channel k for the coupling, channels b, m and o respectively corresponding to crystal b for the upper zone, channel m for the middle zone and channel o for the lower zone in the weld. On the paper a preprinted weld shape 71 is indicated over the channel lines. In the weld 37 a defect 77 is denoted, resulting into indications onto the channel lines m, o, b in that order (FIG. 7a) presuming that the defect in the weld is of such dimensions that it may be detected by the three crystals.

The spacial displacement between the several crystals, already denoted in FIG. 4, may be eliminated. The signal from the crystal m, which is passing first and also the signal from the crystal o, passing thereafter, are delayed, for instance by storing into a shift register, until also the last crystal b has passed the concerned location so that the indications will be shifted in line as indicated in FIG. 7b. The delay rate depends on the width of the probe, i.e. the mutual distance between the crystals and the scanning speed and may be preprogrammed before the inspection starts. The same measure may be used for the transverse defect crystals.

Figure 8A:
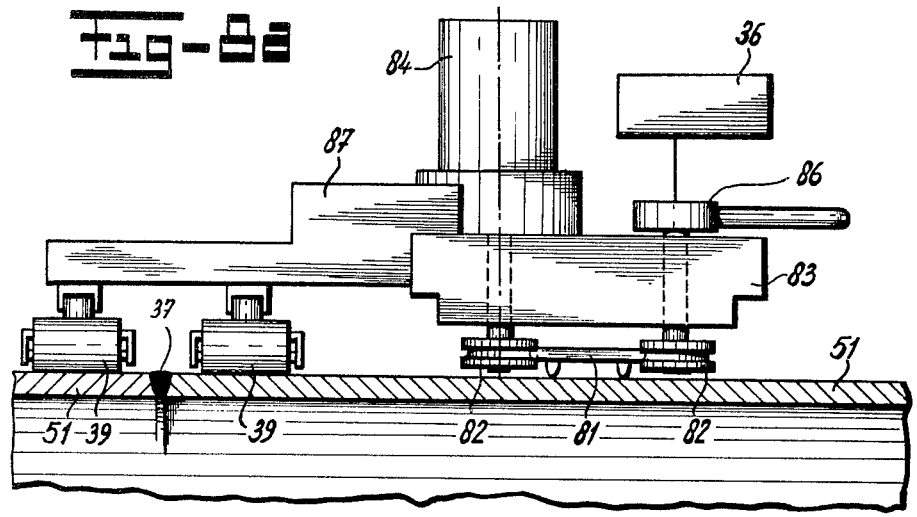
FIG. 8a shows in a side elevation view, partly in section, an example of a manipulator of the band type, whereby the probes are mounted onto a carriage moving along a band or rail.
Figure 8B:
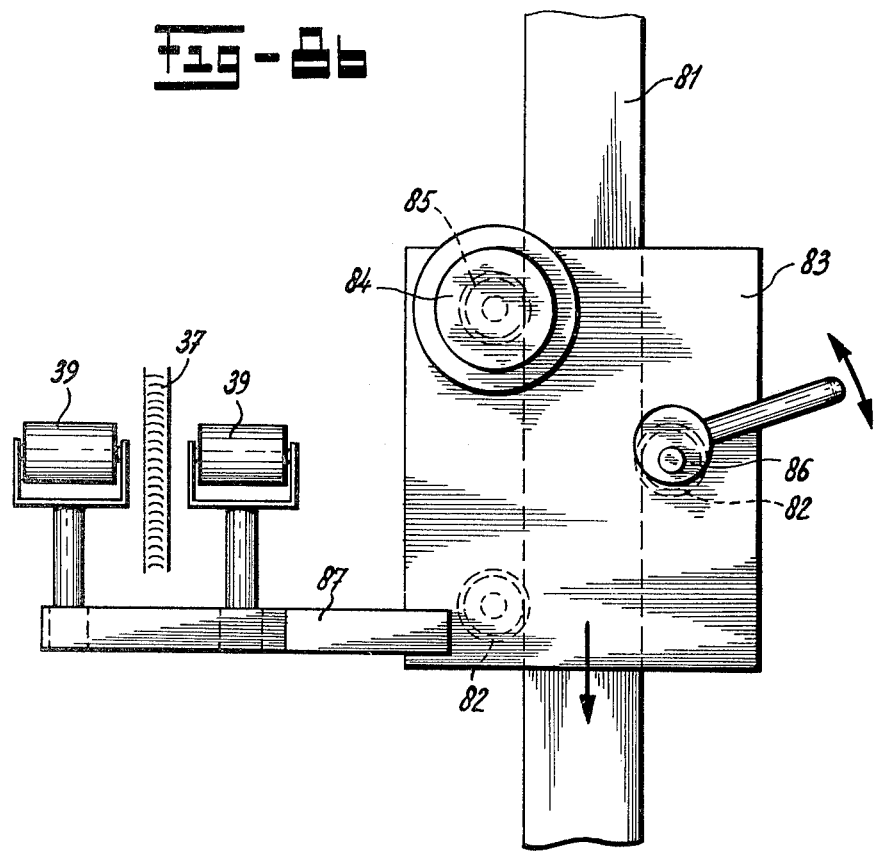

FIG. 8 indicates how a manipulator of the horse shoe type may be replaced by a manipulator of the band or rail type, whereby a probe carriage 83 is moved along the weld 37 controlled by a motor 84 using a band or rail 81 for guiding the wheels 82. The eccentric element 86 supports one of the guide wheels 82 and functions to clamp the probe carriage 83 against the band. A motor 84 mounted on the carriage as seen in FIG. 8, drives a drive wheel 85 to move the carriage. The multi-crystal switch 36 may be mounted onto said probe carriage. Said carriage 83 carries an extending supporting arm or side arm 87 to which two probes 39 are mounted such that said probes may be elastically pressed against the pipe at both sides of the weld 37.

This construction is especially useful when the method according to the invention is used in combination with a mechanized welding method. The same rail or band used for guiding the welding means may also be used for guiding the probe carriage. Such a system is perfectly suitable for fast and objective recording of welding defects.

FIG. 9 illustrates the configuration of the system during the inspection of an on-land pipe line 51, whereby an example is illustrated of a manipulator of the horse shoe type and also of a manipulator of the band type. A kind of crane 40, mounted onto a vehicle 91 is necessary when the embodiment illustrated in FIG. 1 is used, whereby the crane moves the inspecting system in longitudinal direction over the pipe line 51 or the vehicle 91 itself is traveling along the pipe line 51. The main control unit 41 and the ultrasonic device 42 may be, for instance, positioned on said vehicle.

If the manipulator of the band type is used then said manipulator will be controlled by the main control unit 41 and the ultrasonic device 42 for instance positioned on a vehicle 92.

Each vehicle may carry a pipe test segment, for instance the pipe segment 93 on vehicle 91 for calibrating the inspecting system.

Whereas preferred, exemplary embodiments of the invention have been described above, the foregoing descriptions should not be understood to limit the scope of the invention, which scope is set forth in the appended claims.

What is claimed is:

1. System for inspecting circumferentially welded joints in pipe lines and the like using ultrasonic waves, comprising a multi-channel ultrasonic device including switching means for selectively exciting multiple ultrasonic wave generating crystals, manipulation means having a control unit and at least a set of ultrasonic probes, and a recorder, the manipulation means being approximately circular and adapted to be positioned around the pipe line and the set of ultrasonic probes being attached to said manipulation means such that the probes are pressed against the outer wall of the pipe near the welded joint, said probes providing multiple crystals angularly disposed to inspect various portions of the weld which, combined, constitute the entire weld, the crystals in each probe being activated by the multi-channel ultrasonic device through the switching means for transmitting ultrasonic waves into the pipe material and for receiving the reflected waves, which reflected waves are processed by the ultrasonic device and registered by the recorder, the set of ultrasonic probes further including crystals located to direct and receive longitudinal ultrasonic waves reflected from the pipe interior surface to measure pipe thickness, and said switching means comprising means defining gates enabling angled crystals for receipt of transverse ultrasonic waves reflected from weld defects, the gates being timed on the basis of measured thickness, angle of each said transverse wave and its propagation speed in order to avoid recording of reflections due to weld geometry.

2. System for inspecting circumferentially welded joints in pipe lines and the like using ultrasonic waves, comprising a multi-channel ultrasonic device including switching means for selectively exciting multiple ultrasonic wave generating crystals, manipulation means having a control unit and at least a set of ultrasonic probes, and a recorder, the manipulation means being approximately circular and adapted to be positioned around the pipe line and the set of ultrasonic probes being attached to said manipulation means such that the probes are pressed against the outer wall of the pipe near the welded joint, the crystals in each probe being activated by the multi-channel ultrasonic device through the switching means for transmitting ultrasonic waves into the pipe material and for receiving the reflected waves, which reflected waves are processed by the ultrasonic device and registered by the recorder, the manipulation means including a support with interrupted circular shape forming two legs and, carrying a set of ultrasonic probes at each leg in such a position that said sets of ultrasonic probes are positioned diametrically opposite each other and that the manipulation means is carried by a frame, the frame also supporting an auxiliary control unit for controlling movement of the ultrasonic probes by the manipulation means, said manipulator including the support and each set of ultrasonic probes being movable through greater than 180° around the pipe.

3. System for inspecting circumferentially welded joints in pipe lines and the like using ultrasonic waves, comprising a multi-channel ultrasonic device including switching means for selectively exciting multiple ultrasonic wave generating crystals, manipulation means having a control unit and at least a set of ultrasonic probes, and a recorder, the manipulation means being approximately circular and adapted to be positioned around the pipe line and the set of ultrasonic probes being attached to said manipulation means such that the probes are pressed against the outer wall of the pipe near the welded joint, the crystals in each probe being activated by the multi-channel ultrasonic device through the switching means for transmitting ultrasonic waves into the pipe material and for receiving the reflected waves, which reflected waves are processed by the ultrasonic device and registered by the recorder, the manipulation means comprising a guiding band adapted to be positioned around the pipe beside the welded joint, means for guiding a probe carriage along the band including a drive wheel and guide wheels engaging side edges of the band, eccentrically movable means mounted for movement toward and away from the band side edge for clamping the carriage to the band, said carriage having a transversely extending side arm supporting a set of ultrasonic probes said probes being movable around the pipe through greater then 360°.

4. System according to claim 1, 2 or 3, characterized in that each set of ultrasonic probes comprises two probes at a mutual distance fixed to a supporting element and adapted to be pressed against the pipe at both sides of the welded joint, each probe contains plural crystals each assigned to a certain depth zone in the pipe wall, and adapted to transmit and receive ultrasonic waves into and from the pipe material at different angles corresponding with said depth zones.

5. System according to claim 1, 2 or 3, characterized in that the crystals in each probe are positionally and angularly mounted into the probe holder such that the whole volume of the weld and its directly adjacent material is inspected with sufficient sensitivity during timed gates, adjusted to the reception time of defect-reflected waves.

6. System according to claim 5, characterized in that the recorder includes means for recording reflected ultrasonic waves exceeding a previously adjusted recording threshold as one of two indications representing the presence or absence of a defect, of said recording means having multiple recording channels, each recording channel corresponding to one or more crystals, and means for presenting on the paper an indication of the position of the probes along the weld.

7. System according to claim 6, characterized in that the system includes means for electronically time correcting for the spacial displacement of the crystals within the probes such that the indications corresponding to reflections received from a transverse section of the weld are recorded onto the paper in one line.

8. System according to one of the claims 1, 2 or 3, characterized in that, besides reflections resulting from possible defects, said probes include means for directing one or more ultrasonic signals through the weld, and the system further including means for monitoring those through-the-weld transmissions for detecting partial or total disappearance of said signals to give an indication about the presence of one or more sound shielding defects.

9. System according to claim 2 or 3, characterized in that the system includes mobile means for moving the system in the lengthwise direction along the pipe line.

10. System according to claim 1, characterized in that said system includes means for adjusting the path of movement of the probes parallel to the plane of the weld.

11. The method of inspecting circumferentially welded joints in pipe lines and the like using ultrasonic waves, comprising the steps of providing a set of ultrasonic probes including multiple angularly disposed ultrasonic wave generating crystals, locating a manipulator in parallel relation to the weld, moving the probes with respect to the weld by means of the manipulator, selectively exciting the ultrasonic wave generating crystals, by switching crystal excitation signals among the crystals, measuring the thickness of the pipe by determining the time of an ultrasonic longitudinal pulse reflected from the pipe inside surface, selectively receiving reflected transverse waves at the crystals by controlling the crystal reception times relative to the propagation times based on the measured thickness, angle of each transverse wave and its propagation speed and producing a visual indication of the reception by the crystals relative to displacement along the weld, said step of selectively receiving further comprising limiting the reception of ultrasonic reflections so as to exclude reflections from geometric weld features.

* * * * *